US011105005B2

(12) United States Patent
Johansson et al.

(10) Patent No.: US 11,105,005 B2
(45) Date of Patent: Aug. 31, 2021

(54) PRODUCT CONTAINER WITH ELECTROCHEMISTRY DEVICE

(71) Applicant: Colgate-Palmolive Company, New York, NY (US)

(72) Inventors: Patrik Johansson, Hoboken, NJ (US); Venda Porter Maloney, Piscataway, NJ (US); Kelly Duncan, Washington, NJ (US)

(73) Assignee: Colgate-Palmolive Company, New York, NY (US)

( * ) Notice: Subject to any disclaimer, the term of this patent is extended or adjusted under 35 U.S.C. 154(b) by 142 days.

(21) Appl. No.: 16/330,263

(22) PCT Filed: Sep. 7, 2016

(86) PCT No.: PCT/US2016/050519
§ 371 (c)(1),
(2) Date: Mar. 4, 2019

(87) PCT Pub. No.: WO2018/048393
PCT Pub. Date: Mar. 15, 2018

(65) Prior Publication Data
US 2019/0186025 A1    Jun. 20, 2019

(51) Int. Cl.
| | |
|---|---|
| *C25B 15/08* | (2006.01) |
| *C25B 1/30* | (2006.01) |
| *A61Q 11/00* | (2006.01) |
| *C25B 11/02* | (2021.01) |
| *A61K 8/22* | (2006.01) |
| *A61K 8/23* | (2006.01) |
| *C25B 1/04* | (2021.01) |

(Continued)

(52) U.S. Cl.
CPC .............. *C25B 1/30* (2013.01); *A61K 8/22* (2013.01); *A61K 8/23* (2013.01); *A61Q 11/00* (2013.01); *C25B 1/04* (2013.01); *C25B 1/29* (2021.01); *C25B 11/02* (2013.01); *C25B 15/08* (2013.01); *A61C 19/066* (2013.01); *A61K 2800/805* (2013.01); *A61K 2800/83* (2013.01); *A61K 2800/87* (2013.01); *Y02E 60/36* (2013.01)

(58) Field of Classification Search
CPC .......... C25B 15/02; C25B 15/08; C25B 9/00; C25B 9/06; C25B 1/30; C25B 9/12
See application file for complete search history.

(56) References Cited

U.S. PATENT DOCUMENTS

| | | | |
|---|---|---|---|
| 1,681,320 | A | 8/1928 | Bergl et al. |
| 3,478,741 | A | 11/1969 | Simor et al. |

(Continued)

FOREIGN PATENT DOCUMENTS

| | | |
|---|---|---|
| CN | 1435512 | 8/2003 |
| EP | 1533041 | 5/2005 |

(Continued)

OTHER PUBLICATIONS

International Search Report and Written Opinion of the International Searching Authority in International Application No. PCT/US2016/050519, dated Mar. 14, 2017.

*Primary Examiner* — Zulmariam Mendez

(57) ABSTRACT

A product container is provided. The product container includes a first product and an electrochemistry device configured to convert a portion of the first product into a second product, which is an unstable formulation.

15 Claims, 10 Drawing Sheets

(51) Int. Cl.
*C25B 1/29* (2021.01)
*A61C 19/06* (2006.01)

(56) References Cited

U.S. PATENT DOCUMENTS

| | | |
|---|---|---|
| 3,996,126 A | 12/1976 | Rasmussen |
| 5,154,917 A | 10/1992 | Ibrahim et al. |
| 7,515,507 B2 | 4/2009 | Nanda |
| 7,703,226 B2 | 4/2010 | Schnuckle |
| 7,775,795 B2 | 8/2010 | Khawaled et al. |
| 8,156,602 B2 | 4/2012 | Jimenez et al. |
| 8,459,275 B2 | 6/2013 | Rischmiller |
| 8,708,700 B2 | 4/2014 | Jimenez et al. |
| 2009/0008268 A1 | 1/2009 | Salathe et al. |
| 2009/0314651 A1* | 12/2009 | Field .................... C02F 1/4618 205/335 |
| 2016/0322649 A1* | 11/2016 | Swiegers ............ H01M 8/0232 |
| 2017/0367943 A1 | 12/2017 | Johansson et al. |

FOREIGN PATENT DOCUMENTS

| | | |
|---|---|---|
| JP | 2007-044573 A | 2/2007 |
| JP | 2011-160900 A | 8/2011 |
| KR | 20160040801 A | 4/2016 |
| RU | 2051990 | 1/1996 |
| UA | 75594 | 2/2003 |

\* cited by examiner

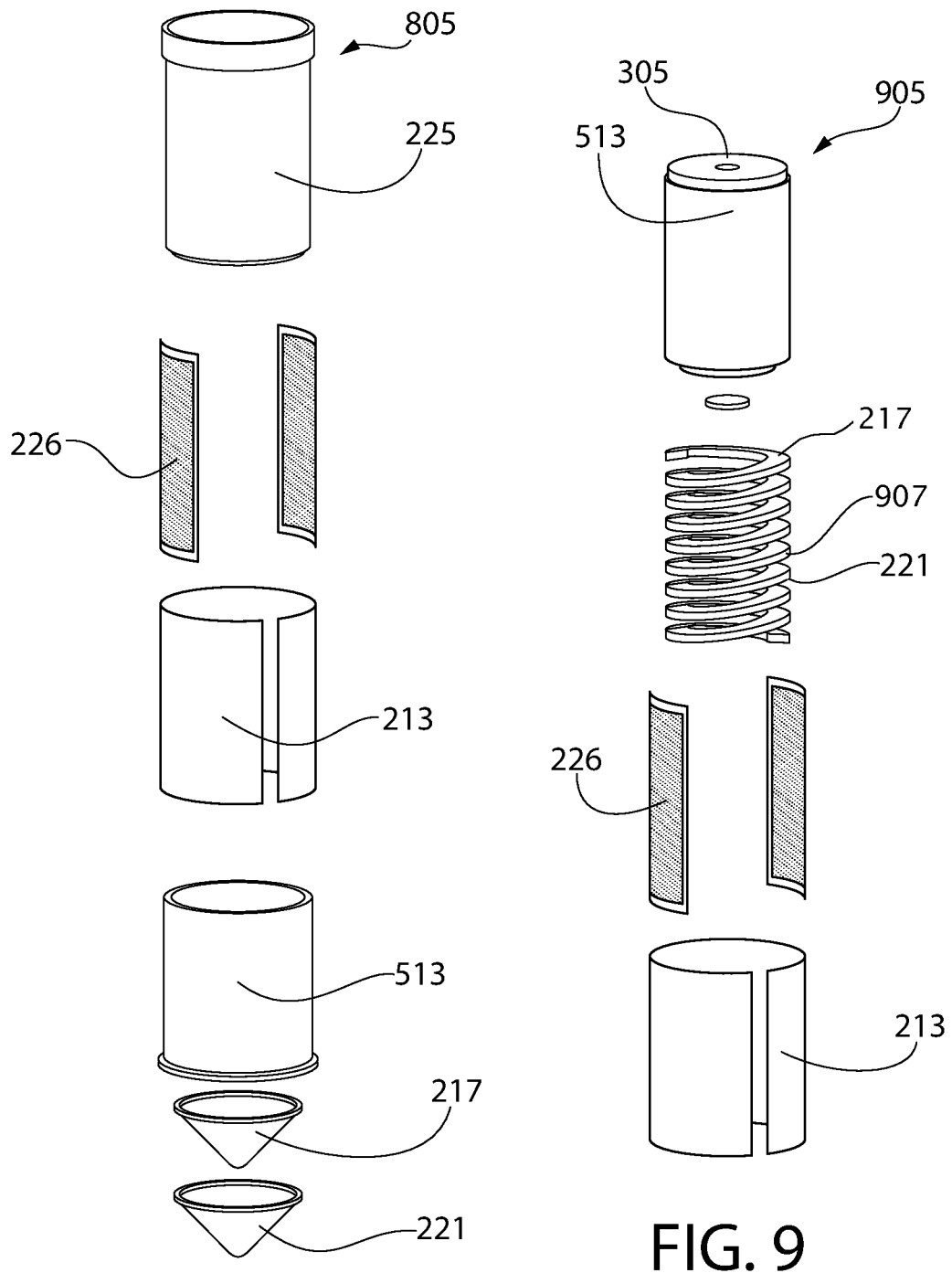

PRODUCT CONTAINER WITH ELECTROCHEMISTRY DEVICE

BACKGROUND

Many consumer products have been developed to address or treat specific consumer needs or concerns. Some of these products may contain ingredients which are difficult to formulate into a stable product that is sufficiently efficacious throughout a typical product lifecycle. For example, oral care products (e.g., dental hygiene products) have been developed to whiten teeth. These products may contain chemistry (e.g., hydrogen peroxide) that can be applied by a consumer, a dentist, or other professional. In some such products, potassium persulfate ($K_2S_2O_8$) may be used to whiten teeth. However, due to the high reactivity of potassium persulfate in aqueous environments, it has poor compatibility with common ingredients used in oral care products. Therefore, potassium persulfate is difficult to formulate into a stable product. Anhydrous and/or hydrophobic formulations may improve the stability of potassium persulfate, but may interfere with release of the persulfate from the formulation, which can result in poor performance.

BRIEF SUMMARY

Implementations consistent with the present disclosure provide a product container including a first product and an electrochemistry device. The electrochemistry device can be configured to convert a portion of the first product into a second product, which is an unstable formulation.

In some implementations, the electrochemistry device can include a dispensing cavity and an electric circuit. The electric circuit can include power source, such as for example, a battery, a first electrode, and a second electrode. The first electrode and the second electrode can be disposed in the dispensing cavity. The electric circuit can be configured to generate the second product from the portion of the first product in the dispensing cavity by outputting power from the power source to the portion of the first product via the first electrode and the second electrode.

In some implementations, the first product can be a liquid, a gel, or a paste. Further, in some implementations, the first product can be an oral care product. Still further, in some implementations, the first product can be a whitening product. In some implementations, the whitening product can be a persulfate. In some implementations, the whitening product can be a peroxide.

In some implementations, the product dispenser includes a bottle including a cap, and the cap houses the electrochemistry device. In some implementations, the cap includes a cup, and an interior of the cup defines the dispensing cavity. Further, in some implementations, the dispensing cavity can include channels passing through the cap. Still further, in some implementations, the product container can include a dip tube extending from the first product to the cap, a first electrode in the dip tube, a second electrode in the cap.

In some implementations, the first product can have a first predetermined pH, and the second product can have a second predetermined pH. In some implementations, the first predetermined pH can be about 3 and the second predetermined pH value can be about 7. Further, in some implementations, the first predetermined pH can be about 11, and the second predetermined pH value can be about 7.

In some implementations, the first electrode and the second electrode can include co-spiraled shapes.

In some implementations, the electronic circuit further includes a switch configured to activate and deactivate the electric circuit. In some implementations, a manual selector can be configured to control the switch. Further, in some implementations the switch can be configured to automatically deactivate the electric circuit based on a predetermined event.

In some implementations, the dispensing cavity includes an agitator powered by the electric circuit. In some implementations, the electric circuit further comprises an indicator.

Further areas of applicability of the present invention will become apparent from the detailed description provided hereinafter. It should be understood that the detailed description and specific examples, while indicating some preferred aspects of the invention, are intended for purposes of illustration only and are not intended to limit the scope of the invention.

BRIEF DESCRIPTION OF THE DRAWINGS

The present invention will become more fully understood from the detailed description and the accompanying drawings, wherein:

FIG. 8 illustrates an exploded perspective view of an exemplary electrochemistry device in accordance with aspects of the present disclosure;

FIG. 9 illustrates an exploded perspective view of an exemplary electrochemistry device in accordance with aspects of the present disclosure;

DETAILED DESCRIPTION

The present disclosure is generally directed to packaging, and more particularly to containers and dispensers for consumer products. Exemplary implementations of product containers and dispensers in accordance with aspects of the present disclosure include electrochemistry devices that produce highly reactive products in situ from one or more products stored in the product container. The products can be stable for long periods of time (e.g., months), whereas the reactive products may only be stable for short periods of time (e.g., seconds or minutes). The use of in situ production of the reactive product avoids the challenges of formulating and stabilizing such products for storage for extended time periods, which can affect the efficacy and their marketability, such as described above.

Electrochemistry devices in accordance with aspects of the present disclosure can be selectively activated to substantially change a pH of a product stored in a product container. For example, in some cases the product container may store a product (e.g., hydrogen peroxide-based mouthwash) having a pH of 3, at which it is stable for long periods of time (e.g., months). At the time and place of use, a user may activate an electrochemistry device in the product container, which induces a chemical reaction that raises the pH of the product from 3 to 7 and produces a reactive product. In some implementations, electrodes of the electrochemistry device induce the formation of the reactive product. Additionally alternatively, the electrodes contribute a component of the reactive product. The efficacy of the reactive product can be substantially greater than that of a stable and/or low-pH product (e.g., improved whitening of teeth and killing microbes). However, the reactive product may be unstable such that its performance degrades in a short period of time (e.g., minutes).

In addition, electrochemistry devices in accordance with aspects of the present disclosure can include indicators (e.g., a light-emitting device and/or a sound-emitting device) that are activated in association with the in situ production of the reactive product from the products to provide cueing and/or feedback to users (e.g., consumers). Such cueing allows for an attractive and interesting method for providing users with feedback regarding the operation of the electrochemistry devices and the state of the product. For example, the indicator can be used to signal to the user an amount of time the product should remain in the electrochemistry device before being dispensed.

Figures 1A, 1B:
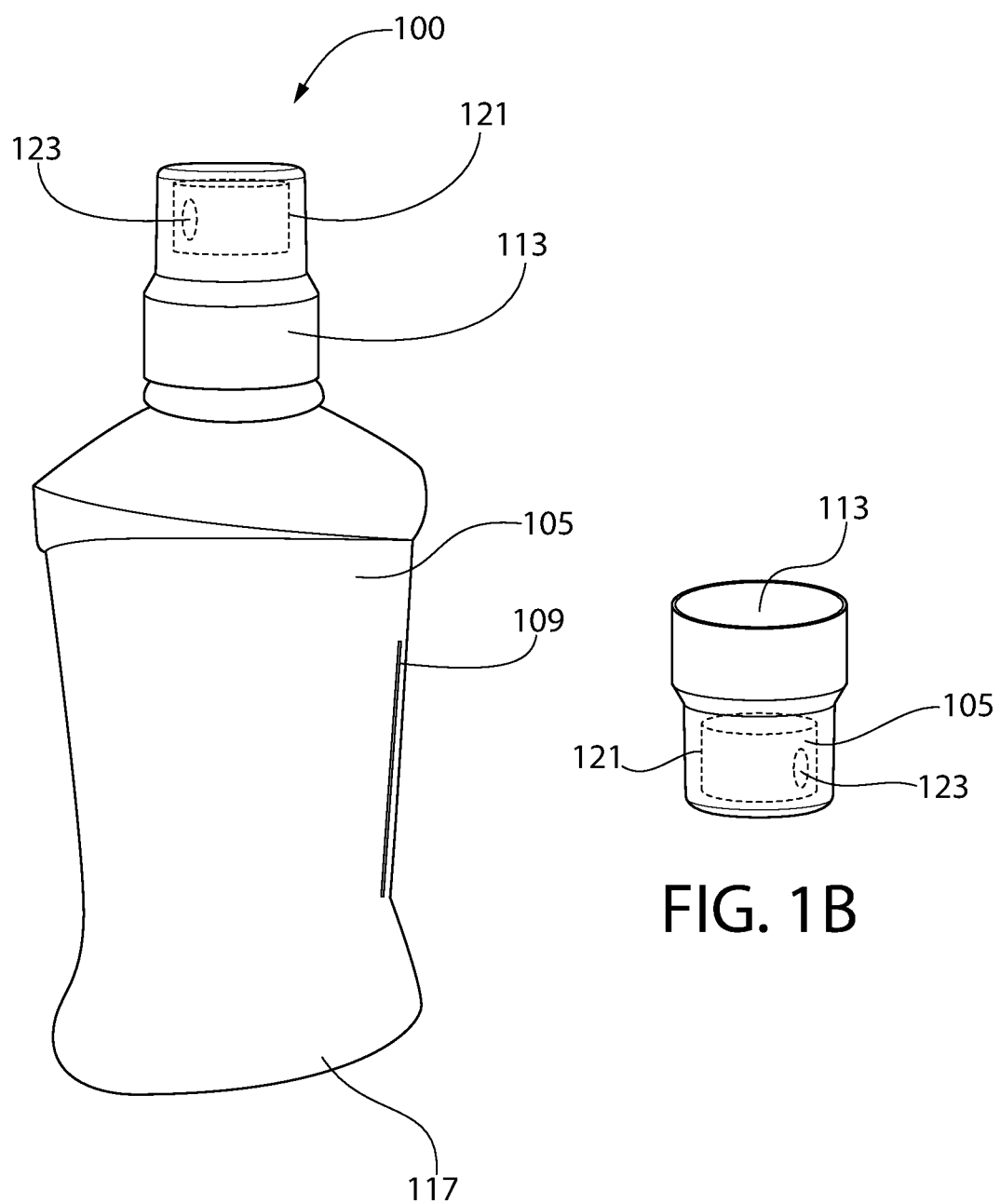
FIG. 1A illustrates a side perspective view of an exemplary product container in accordance with aspects of the present disclosure.
FIG. 1B illustrates a side perspective view of an exemplary cap for a product container in accordance with aspects of the present disclosure.

FIG. 1A illustrates a side perspective view of an exemplary container 100 in accordance with aspects of the present disclosure. The container 100 is a vessel that stores a product 105, which can be an electrically conductive liquid, gel, paste, semi-solid, or the like. In implementations, the container 100 can be a bottle, jar, or tube, and the product 105 can be an oral care product (e.g., mouthwash, toothpaste, or whitening agent) or a cleaning product (e.g., soap or detergent). The container 100 is comprised of a sidewall 109 closed by a cap 113, and a bottom 117 that retain the product 105 in the vessel. In some implementations, the cap 113 can be detachable. For example, the cap 113 can have a cup shape that is threaded onto a mouth of the container 100. In other implementations, the cap 113 is not detached for dispensing. Rather, the cap 113 can be permanently or semi-permanently connected to or integrated with the sidewall 109 and include a spout or valve for dispensing the product 105.

The container 100 also includes an electrochemistry device 121 that converts the product 105, which is substantially stable, to a reactive product, which is unstable relative to the product 105. In some implementations, the electrochemistry device 121 is entirely contained within the cap 113. In accordance with aspects of the present disclosure, the electrochemistry device 121 causes a chemical change in the product 105 to generate the reactive product at the time of use (e.g., "in situ"). As used herein, the term "stable" means that the chemical properties of at least 70% of the active ingredients in a formulation or compound will remain substantially unchanged after being stored for at least two (2) months at room temperature (e.g., about 65-80 degrees Fahrenheit). Also, as used herein, "unstable" means that the active ingredients of a formulation or compound will degrade and become substantially ineffective within a short period of time. In implementations, the short period of time is less than about 30 minutes. In some implementations (e.g., mouthwash or cleaning products), the short period of time can be between about 2 minutes to about 5 minutes. In other implementations (e.g., a whitening agent), the short period of time may be less than 60 seconds.

The electrochemistry device 121 can also include an indicator 123 for providing visual and/or audible cues to a user. In some implementations, the indicator 123 is exposed on an external surface of the container 100 or the cap 113. In other implementations, the indicator 123 is entirely internal to the container 100 or the cap 113 such that it illuminates the product 105. The cues provided by the indicator 123 can be associated with the conversion of the product 105, as well as for providing entertaining displays. For example, the indicator 123 may produce a first indication while the electrochemistry device 121 is converting the product 105 and a second indication (e.g., after a timer of the electrochemistry device 121 determines a predetermined amount of time or after a sensor of the electrochemistry device 121 detects a pH) to indicate that the conversion of the product 105 to an reactive product is complete.

In an exemplary usage example, the product container 100 can be a mouthwash bottle having a cup-shaped cap 113, and the product 105 can be a precursor for a mouthwash formulation including a whitening agent (e.g. hydrogen peroxide). A user (e.g., a consumer) can remove the cap 113 by unscrewing it from the container 100 and dispense a portion of the product 105 into the cap 113. For example, FIG. 1B illustrates a side perspective view of the exemplary cap 113 including the portion of the product 105 and the electrochemistry device 121. The electrochemistry device 121 can be activated (automatically or manually) to convert the product 105 into the reactive product by, for example, changing the pH. In implementations, the electrochemistry device 121 outputs a current of about 500 mA over a period of about 30 seconds to about 60 seconds to convert the product 105. Additionally, during the period when the electrochemistry device 121 is activated, the indicator 123 can output one or more audio and/or visual cues indicating that the conversion of the product 105 is occurring and/or complete. For example, the electrochemistry device 121 can illuminate the product 105 using one or more colored or non-colored light-emitting diodes ("LEDs"). After determining that the conversion is complete (e.g., based on time, pH, or temperature), the electrochemistry device 121 can provide a different cue (visual and/or audio) using the indictor 123. The user can then use the reactive product that was generated in the cap 113 from the product 105.

Figure 2:
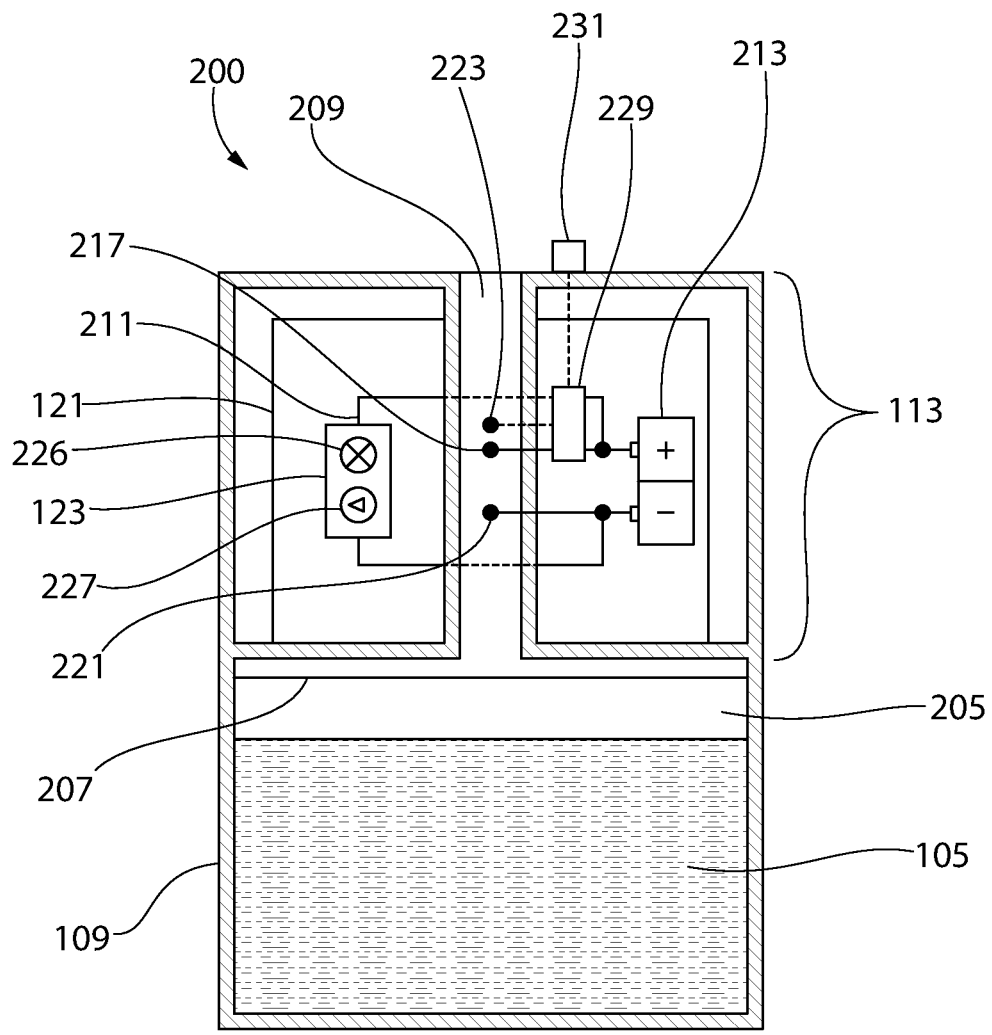
FIG. 2 illustrates functional block diagram of an exemplary product container in accordance with aspects of the present disclosure.

FIG. 2 illustrates a functional block diagram of an exemplary container 200 in accordance with aspects of the present disclosure. The container 200 includes a product 105, a cap 113, and an electrochemistry device 121, which can be the same or similar to those of the container previously described herein (e.g., container 100). The container 200 and/or the cap 113 can be formed from transparent or translucent material (e.g., clear or semi-clear plastic). In implementations, the cap 113 is integral with the container 200. In other implementations, the cap 113 can be removable from the container 200 and house the electrochemistry device 121. In implementations, the product 105 is separated from the electrochemistry device 121 by a void 205, which avoids contact between the product 105 and the electrochemistry device 121 when the container 200 is not in use. The void 205 can be maintained during shipping and storage of the container 200 by a removable seal 207 (e.g., foil) located under the cap 113.

The electrochemistry device 121 includes a dispensing cavity 209 and an electric circuit 211. The dispensing cavity 209 can hold the portion of the product 105 dispensed by the user into the cap 113. In implementations, the dispensing cavity 209 can have cup shape (e.g., an open vessel) for holding the product 105, such as illustrated in FIG. 1B. In implementations, the dispensing cavity 209 is a channel passing through the electrochemistry device 121. For example, a bottom of the dispensing cavity 209 can be defined by a top wall of the cap 113, and the sidewall of the dispensing cavity 209 can be defined by an interior wall of the electrochemistry device 121.

The electric circuit 211 of the electrochemistry device 121 includes a power source 213, an electrode 217, and an electrode 221. Additionally, in some implementations the electrochemistry device 121 includes an indicator 123 (e.g., light, sound, music, voice instructions, or vibration), a switch 229, a selector 231, and/or a sensor 233. The power source 213 can be a battery, a piezoelectric power generator, a micro-electromechanical power generator, or a solar cell, which can output a direct or alternating current. In some implementations, the power source 213 is a button cell battery, such as a watch battery.

The electrodes 217 and 221 are electrical conductors connected to opposite terminals (e.g., the anode and cathode) of the power source 213. The electrodes 217 and 221 can be comprised of, for example, nickel, carbon, platinum, stainless steel, boron doped diamond, silver, gold, or iron. In implementations, the electrodes 217 and/or the electrode 221 contributes to the conversion of the product 105 by degrading when exposed to the product 105. While the electrodes 217 and 221 are illustrated a nodes for the sake of simplicity, it is understood that the electrodes 217 and 221 can have different shapes and geometries that maximize their surface area in the dispensing cavity. For example, the electrodes 217 and 221 can formed as plates, meshes, coils, spirals, fans, or any other conceivable shape as described herein below.

At least a portion of each of the electrodes 217 and 221 directly contacts or extends into the dispensing cavity 209 without electrically contacting one another. As such, when the dispensing cavity 209 is empty (e.g., substantially devoid of the product 105), an open circuit exists between the electrodes 217 and 221 such that substantially no electrical current is conducted through the electrodes 217 and 221. On the other hand, when a portion of the product 105 is present in the dispensing cavity between the electrodes 217 and 221, a path around the electric circuit 211 can be completed to conduct current from the power source 213 through the electrodes 217 and 221 via the portion of product 105 in the dispensing cavity 209.

The indicator 123 can include a lamp 226 and an alarm 227 (e.g., buzzer or beeper). In implementations, the lamp 226 can be a light emitter that operates over a frequency range between about 300 nm and about 900 nm. For example, the lamp 226 can be a LED, a printed LED, a thin-film LED, a discrete LED, or an organic LED.

The switch 229 can selectively open and close the electric circuit 211 between the power source 213 and the electrodes 217, 221 to selectively conduct electric current through the product 105. In some implementations, the switch 229 is manually operable by a user to close via the selector 231 (e.g., a button or a throw-switch) on the outer surface of the container 200 (e.g., on sidewall 109 or cap 113). For example, the user can dispense a portion of the product 105 into the cap 113 and manually operate the selector 231 to apply power from the power source 213 to the product 105 in the cap 113. After a predetermined amount of time (e.g., about 10 seconds to about 30 seconds), the user can release the selector 231, which opens the switch 229 and cuts power to the electrodes 217 and 221. Additionally, in some implementations, the switch 229 automatically cuts (e.g., removes) the power applied from the power source 213 to electrodes 217 and 221. For example, the switch 229 can automatically open based on a predetermined event. The predetermined event can be an amount of time, a predetermined pH (e.g., conductivity) of the reactive product in the dispensing cavity 209 determined by a sensor 233, or temperature of the reactive product in in the dispensing cavity 209 determined by the sensor 233.

Figure 3:
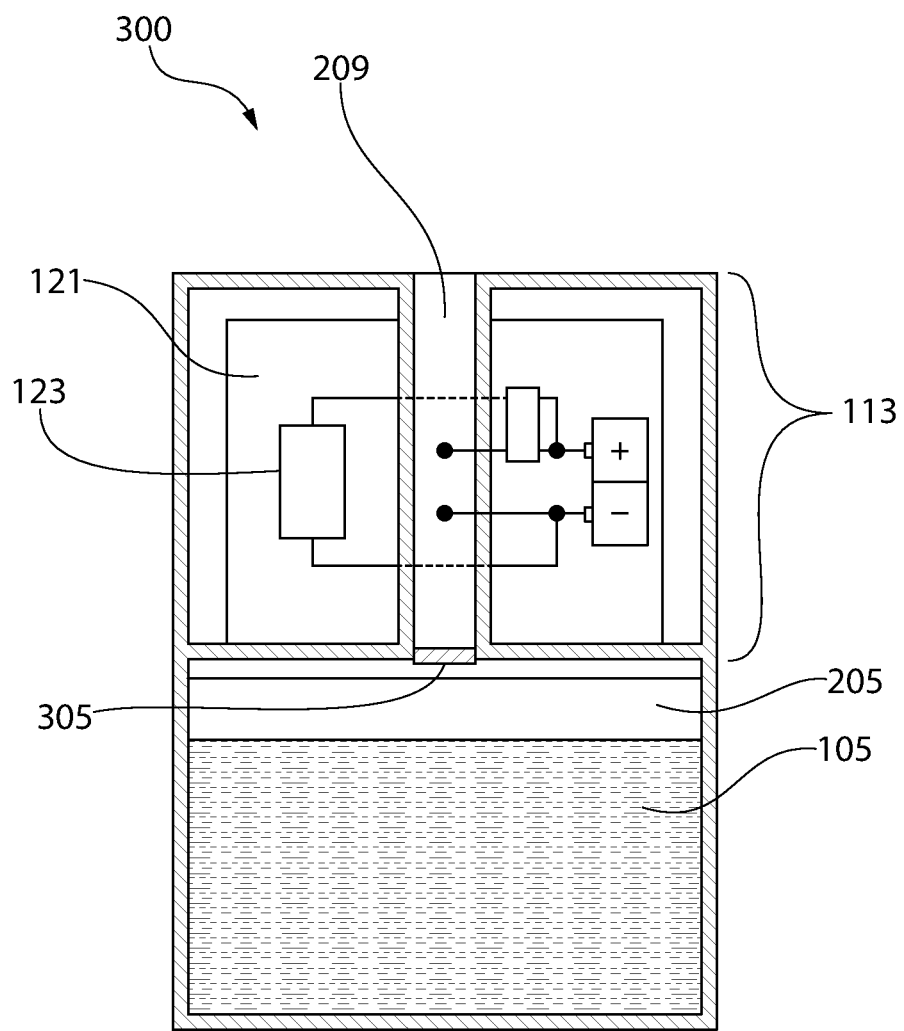
FIG. 3 illustrates functional block diagram of an exemplary product container in accordance with aspects of the present disclosure.

FIG. 3 illustrates a functional block diagram of an exemplary container 300 in accordance with aspects of the present disclosure. The container 300 includes a product 105, a cap 113, and an electrochemistry device 121, which can be the same or similar to those of the containers previously described herein. In implementations, the cap 113 may be permanently or semi-permanently affixed to the container 300. Additionally, the cap 113 can include a valve 305 that control flow of the product 105 through the dispensing cavity 209 and out of the cap 113. In such implementations, the valve 305 can be a one way valve and the dispensing cavity 209 can be one or more channels passing entirely through the cap 113. The valve 305 can be in fluid communication with the dispensing cavity 209 and prevent backflow therefrom.

In a usage example, a user can invert or squeeze the container 300 to cause a portion of the product 105 to cross the void space 205 and enter the dispensing cavity 209 via the valve 305, which prevents backflow of the product 105. Thus, the portion of the product 105 pools in the dispensing cavity 209, where it can be converted into a reactive product by the electrochemistry device 121 as previously described herein. After the conversion is complete, e.g., as indicated by the indicator 123, the user can dispense and use the reactive product.

Figure 4:
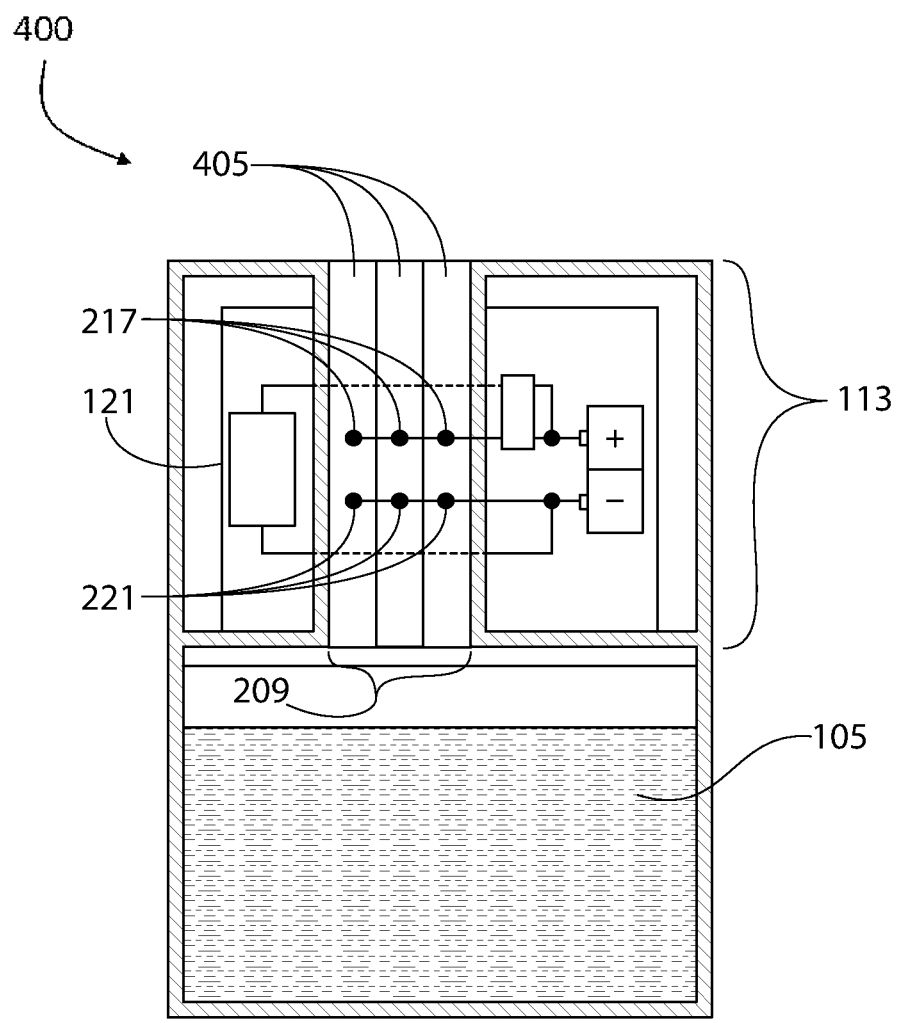
FIG. 4 illustrates functional block diagram of an exemplary product container in accordance with aspects of the present disclosure.

FIG. 4 illustrates a functional block diagram of an exemplary container 400 in accordance with aspects of the present disclosure. The container 400 includes a product 105, a cap 113, and an electrochemistry device 121, which can be the same or similar to those of the containers previously described herein. Additionally, in implementations, the container 400 includes a dispensing cavity 209 comprised of a number of adjacent channels 405. Each of the channels 405 can pass entirely through the cap 113 and be in fluid communication with the product 105 in the container 400. Further, each of the channels 405 can include respective pairs of electrodes 217 and 221. By using multiple channels 405 and multiple electrodes 217, 221, the electrochemistry device 121 may convert the product 105 to a reactive product more quickly. For example, a user may squeeze or invert the container 400, which forces the product 105 through the channels 405. As the product 105 passes through the channels 405, it is induced to form a reactive product, which is dispensed from the cap 113 without having to be retained in the cap 113 for any longer time than is required to traverse the cap 113.

Figure 5A:
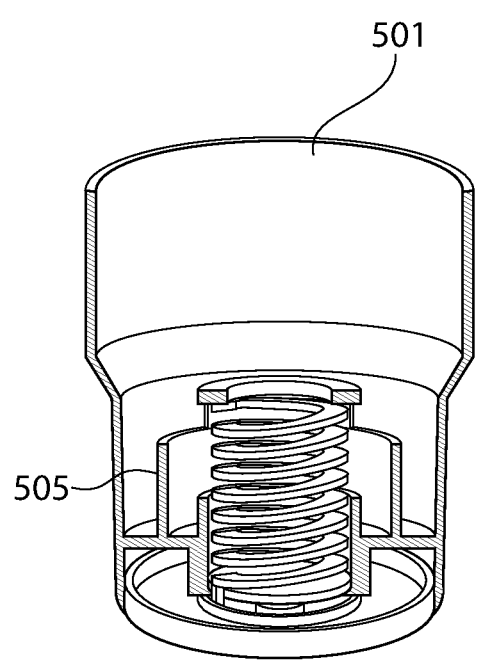
FIG. 5A illustrates a cutaway side perspective view of an exemplary cap including an electrochemistry device in accordance with aspects of the present disclosure.
Figure 5B:
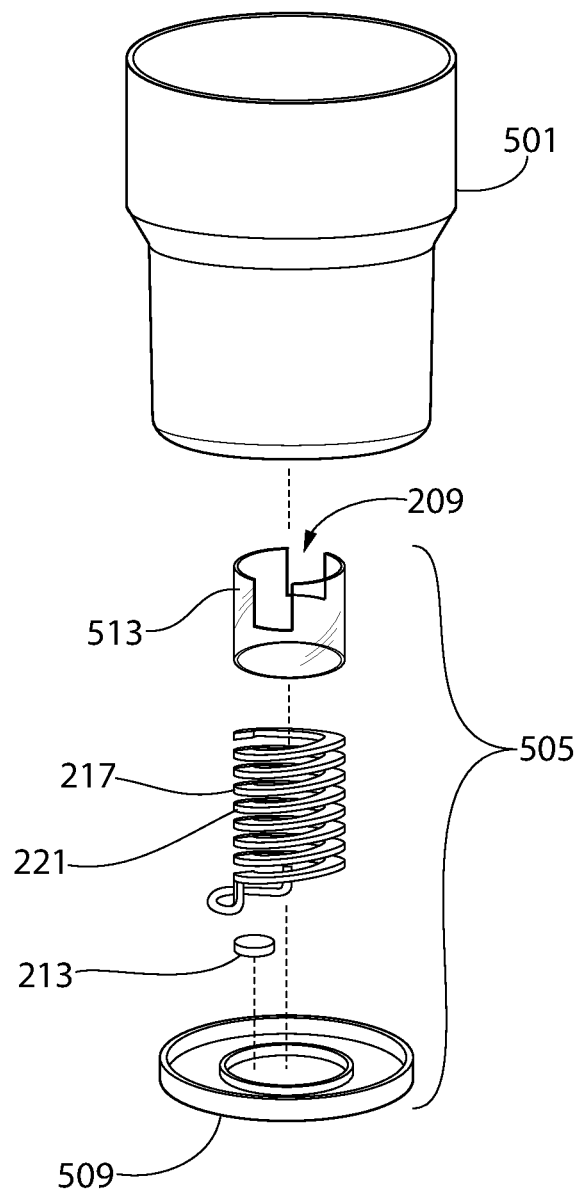
FIG. 5B illustrates an exploded perspective view of an exemplary cap including an electrochemistry device in accordance with aspects of the present disclosure.

FIG. 5A illustrates a cutaway side perspective view of an exemplary cap 501 including an electrochemistry device 505 in accordance with aspects of the present disclosure. FIG. 5B illustrates an exploded perspective view of the cap 501 and the electrochemistry device 505. The cap 501 and the electrochemistry device 505 can be the same or similar to those previously describe herein. Additionally, the electrochemistry device 505 includes a power source 213 and co-spiraled electrodes 217, 221, which can be also the same or similar to those previously described herein. In such implementations, the co-spiraled electrodes 217, 221 can form two parallel electrical paths that spiral along a common axis. Further, the electrochemistry device 505 includes a base 509 and housing 513, which can form a vessel within the cap 501. The interior volume of the vessel can be a dispensing cavity 209, as previously described herein.

Figure 6A:
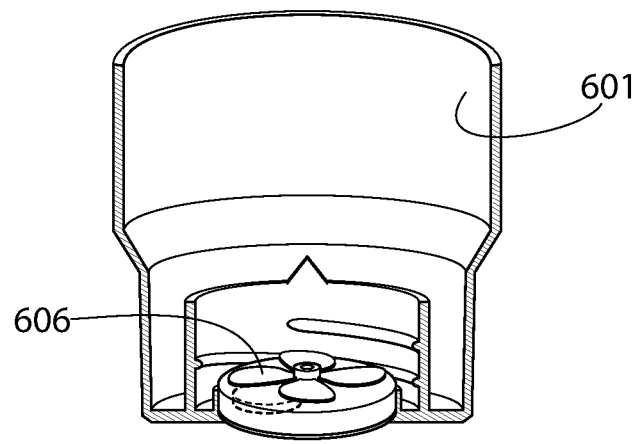
FIG. 6A illustrates a cutaway side perspective view of an exemplary cap including an electrochemistry device in accordance with aspects of the present disclosure.
Figure 6B:
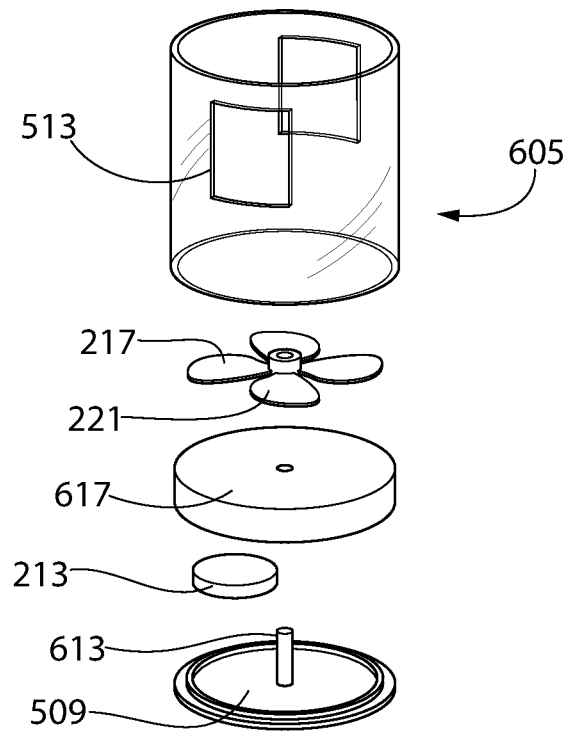
FIG. 6B illustrates an exploded perspective view of an exemplary electrochemistry device in accordance with aspects of the present disclosure.

FIG. 6A illustrates a cutaway side perspective view of an exemplary cap 601 including an electrochemistry device 605 in accordance with aspects of the present disclosure. FIG. 6B illustrates an exploded perspective view of the electrochemistry device 605. The cap 601 and the electrochemistry device 605 can be the same or similar to those previously describe herein. Additionally, the electrochemistry device 605 includes a power source 213 and electrodes 217, 221, which can also be similar to those previously described herein. Further, the electrochemistry device 505 includes a base 509 and housing 513, which can form a vessel within the cap 501. The electrodes 217 and 221 can be formed as fan shapes that fit in the interior volume of the housing 513 and rotate on an axle 613 under power of motor 617, which is driven by the power source 213 to agitate liquid (e.g., product 105) in the cap 601.

Figures 7A, 7B:
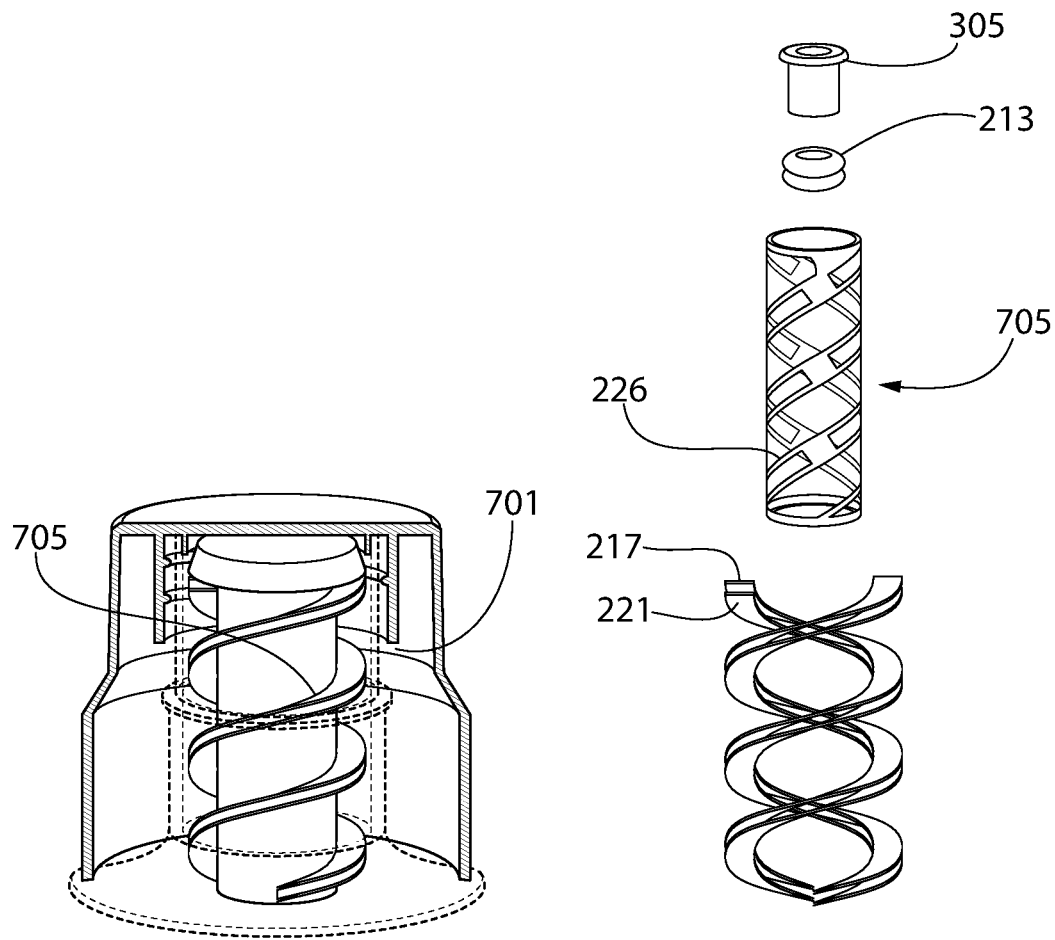
FIG. 7A illustrates a cutaway side perspective view of an exemplary cap including an electrochemistry device in accordance with aspects of the present disclosure.
FIG. 7B illustrates an exploded perspective view of exemplary electrodes in accordance with aspects of the present disclosure.

FIG. 7A illustrates a cutaway side perspective view of an exemplary cap 701 including an electrochemistry device 705 in accordance with aspects of the present disclosure. FIG. 7B illustrates an exploded perspective view of the electrochemistry device 705. The cap 701 and the electrochemistry device 705 can be the same or similar to that previously describe herein. Additionally, the electrochemistry device 705 includes a power source 213, electrodes 217, 221, a lamp 226, and a valve 305, which can also be similar to those previously described herein. The electrodes 217 and 221 can be formed as flat, co-spiral shapes that wrap around a spiral dielectric support 709. The electrodes 217, 221 and the spiral dielectric support 709 can fit in the interior volume of the cap 701. In implementations, the indicator 123 is a lamp 226 formed from a flexible LED that is wrapped in a spiral around the dielectric support 709.

FIG. 8 illustrates an exploded perspective view of an exemplary electrochemistry device 805 in accordance with aspects of the present disclosure. The electrochemistry device 805 includes a power source 213, electrodes 217, 221, a lamp 226, and a housing 513, which can be also be similar to those previously described herein. The power source 213 can be a flexible battery mounted to a sidewall of the housing 513. The electrodes 217, 221 can be mesh conductors and can have cone shapes nested within the housing 513 and offset from one another by a gap. The lamp 226 can be is a flexible LED mounted to a sidewall of the housing 513.

FIG. 9 illustrates an exploded perspective view of an exemplary electrochemistry device 905 in accordance with aspects of the present disclosure. The electrochemistry device 905 includes a power source 213, electrodes 217, 221, a lamp 226, a valve 305, and a housing 513, which can be also be similar to those previously described herein. The power source 213 can be a flexible battery mounted to a sidewall of the housing 513. The electrodes 217, 221 can be co-spiral conductors, as previously described herein. For example, a dielectric material 907 can separate spiral conductors comprising the electrodes 217 and 221, wherein the electrode 217 can be disposed on an upper surface of the dielectric 907 and the electrode 221 can be disposed on the lower surface of the dielectric 907. In implementations, the lamp 226 is a flexible LED mounted to an exterior sidewall of the housing 513.

Figures 10A, 10B:
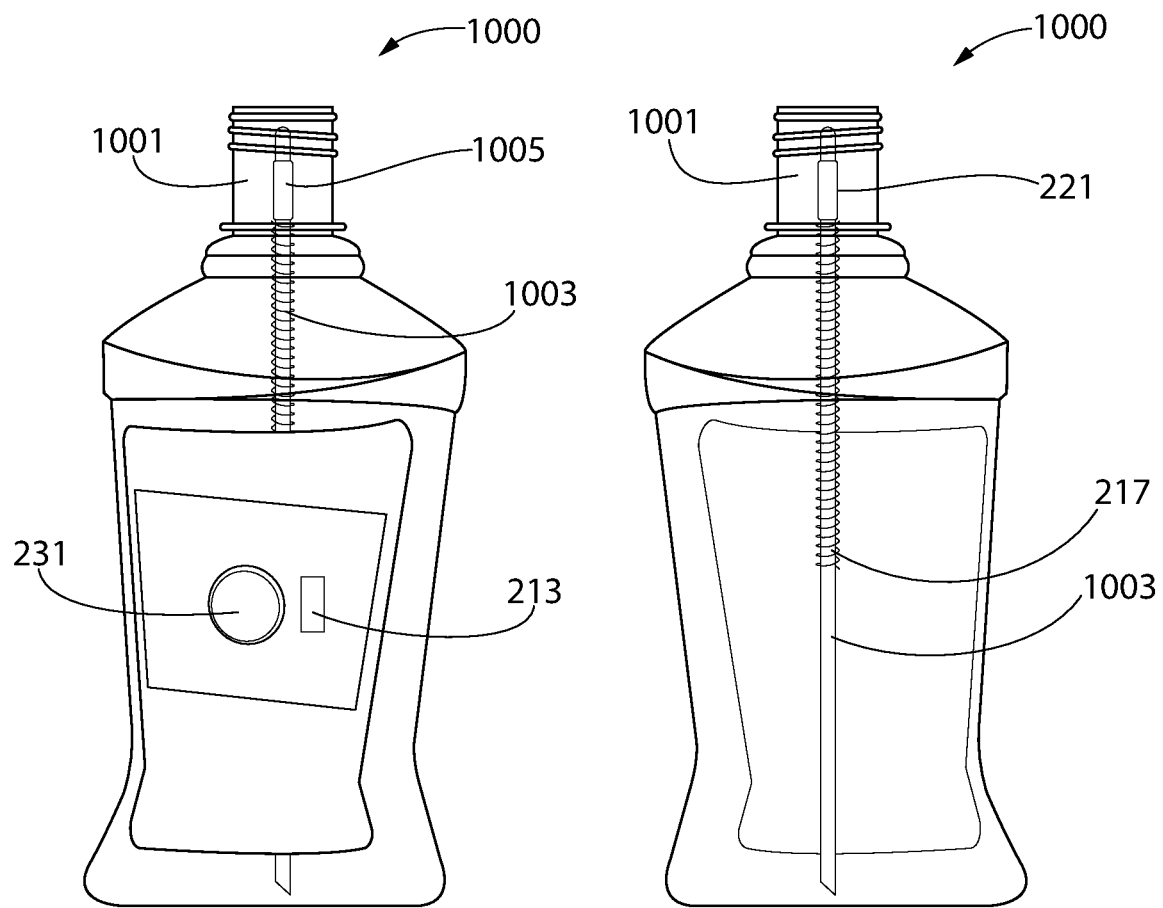
FIG. 10A illustrates a side perspective view of an exemplary product container in accordance with aspects of the present disclosure.
FIG. 10B illustrates a side perspective view of an exemplary product container in accordance with aspects of the present disclosure.
Figure 10C:
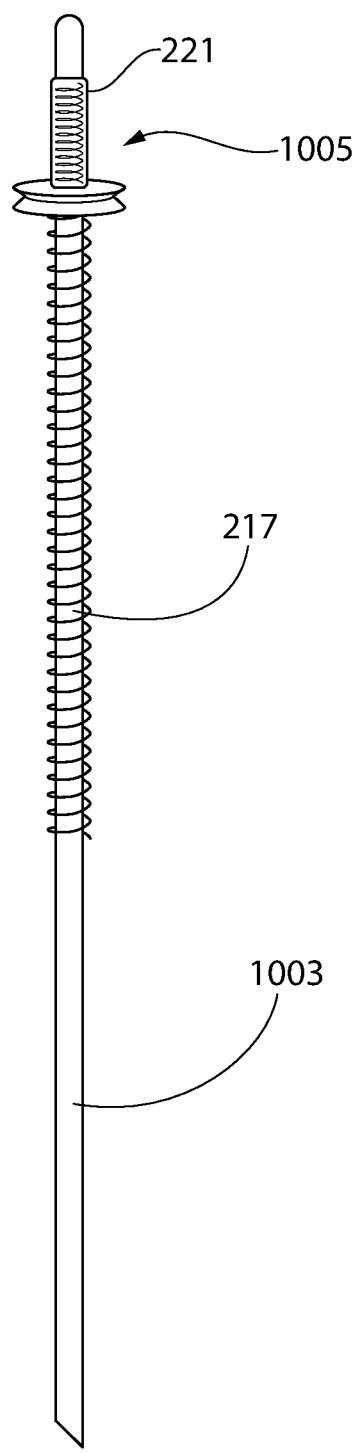
FIG. 10C illustrates a side perspective view of an exemplary electrochemistry device in accordance with aspects of the present disclosure.

FIG. 10A illustrates a front perspective view of an exemplary product container 1000 including a bottle neck 1001, a dip tube 1003 and an electrochemistry device 1005 in accordance with aspects of the present disclosure. FIG. 10B illustrates a rear perspective view of the product container 1000. FIG. 10C illustrates a side perspective view of the exemplary dip tube 1003 and electrochemistry device 1005 in accordance with aspects of the present disclosure. The electrochemistry device 1005 can be similar to that previously described herein. The electrochemistry device 1005 includes a power source 213 (e.g., a battery), a selector 231 (e.g., a button), and electrodes 217, 221 forming an electric circuit (e.g. electric circuit 211), which can be the same or similar to those previously described herein. Additionally, the dip tube 1003 can include the electrode 217 coiled inside the dip tube 1013 and extend to the bottle neck 1001. The electrode 217 provides an electrical signal path from the power source 213 and the selector 231 to the electrode 221 in the electrochemistry device 1005.

The forgoing description of various preferred aspect(s) is merely exemplary in nature and is in no way intended to limit the invention, its application, or uses. The above features have been described in detail with particular reference to certain preferred embodiments thereof, but it will be understood that variations and modifications can be effected within the spirit and scope of the disclosure. One of skill in the art will appreciate that each of the above are exemplary implementations and are not to be construed as a limitation on the scope of the present disclosure.

As used throughout, ranges are used as shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in any ensuing claims are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A product container, comprising:
   a first product;
   an electrochemistry device configured to convert a portion of the first product into a second product, wherein the second product is an unstable formulation,
   a bottle including a bottle neck and a cap;
   a dip tube extending from the first product to the bottle neck,
   a first electrode in the dip tube; and
   a second electrode in the bottle neck.

2. The product container of claim 1, wherein the electrochemistry device comprises:
   a dispensing cavity; and
   an electric circuit comprising a power source wherein:
   the electric circuit is configured to generate the second product from the portion of the first product in the dispensing cavity by outputting power from the power source to the portion of the first product via the first electrode and the second electrode.

3. The product container of claim 1, wherein the first product is a liquid, a gel, or a paste.

4. The product container of claim 3, wherein the first product is an oral care product.

5. The product container of claim 4, wherein the first product is a whitening product.

6. The product container of claim 5, wherein the whitening product is a persulfate.

7. The product container of claim 5, wherein the whitening product is a peroxide.

8. The product container of claim 1, wherein:
   the first product has a first predetermined pH; and
   the second product has a second predetermined pH.

9. The product container of claim 8, wherein the first predetermined pH is about 3 and the second predetermined pH value is about 7.

10. The product container of claim 8, wherein the first predetermined pH is about 11 and the second predetermined pH value is about 7.

11. The product container of claim 2, wherein the electronic circuit further comprises a switch configured to activate and deactivate the electric circuit.

12. The product container of claim 11, further comprising a manual selector configured to control the switch.

13. The product container of claim 11, wherein the switch is configured to automatically deactivate the electric circuit based on a predetermined event.

14. The product container of claim 2, wherein the dispensing cavity comprises an agitator powered by the electric circuit.

15. The product container of claim 2, wherein the electric circuit further comprises an indicator.

* * * * *